(12) United States Patent
Santhanam et al.

(10) Patent No.: US 8,901,122 B2
(45) Date of Patent: *Dec. 2, 2014

(54) COLLAGEN STIMULATORS AND THEIR USE IN THE TREATMENT OF SKIN

(71) Applicant: Avon Products, Inc., Suffern, NY (US)

(72) Inventors: Uma Santhanam, Tenafly, NJ (US); Permanan Raaj Khusial, Highland Mills, NY (US)

(73) Assignee: Avon Products, Inc., New York, NY (US)

( * ) Notice: Subject to any disclaimer, the term of this patent is extended or adjusted under 35 U.S.C. 154(b) by 89 days.

This patent is subject to a terminal disclaimer.

(21) Appl. No.: 13/721,491

(22) Filed: Dec. 20, 2012

(65) Prior Publication Data

US 2014/0179641 A1 Jun. 26, 2014

(51) Int. Cl.

| | | |
|---|---|---|
| *A61K 31/53* | (2006.01) | |
| *A61K 8/49* | (2006.01) | |
| *A61K 8/365* | (2006.01) | |
| *A61K 8/368* | (2006.01) | |
| *A61K 8/67* | (2006.01) | |
| *A61Q 19/00* | (2006.01) | |
| *A61Q 19/08* | (2006.01) | |
| *C07D 401/06* | (2006.01) | |

(52) U.S. Cl.
CPC .............. *A61K 8/4966* (2013.01); *A61K 8/365* (2013.01); *A61K 8/368* (2013.01); *A61K 8/671* (2013.01); *A61Q 19/00* (2013.01); *A61Q 19/007* (2013.01); *A61Q 19/08* (2013.01); *C07D 401/06* (2013.01)
USPC ...................................................... 514/242

(58) Field of Classification Search
USPC ....................................................... 514/242
See application file for complete search history.

(56) References Cited

U.S. PATENT DOCUMENTS

| | | | |
|---|---|---|---|
| 4,081,267 | A | 3/1978 | Hashimoto et al. |
| 7,271,167 | B2 | 9/2007 | Qian et al. |
| RE41,278 | E | 4/2010 | Yu et al. |
| RE41,339 | E | 5/2010 | Yu et al. |
| 2010/0286278 | A1 | 11/2010 | Schehlmann et al. |

OTHER PUBLICATIONS

Van Der SLOTt, A.J., A.-M. Zuurmond, A.F.J. Bardoel, C. Wijmenga, H.E.H. Pruijs, D.O. Sillence, J. Brinckmann, D.J. Abraham, C.M. Black, N. Verzijl, J. DeGroot, R. Hanemaaijer, J.M. TeKoppele, T.W.J. Huizinga, and R.A. Bank. 2003. Identification of PLOD2 as Telopeptide Lysyl Hydroxylase, an Important Enzyme in Fibrosis. Journal of Biological Chemistry. 278:40967-40972.
Walker, L.C., M.A. Overstreet, and H.N. Yeowell. 2005. Tissue-specific expression and regulation of the alternatively-spliced forms of lysyl hydroxylase 2 (LH2) in human kidney cells and skin fibroblasts. Matrix Biology. 23:515-523.
Wu, J., D.P. Reinhardt, C. Batmunkh, W. Lindenmaier, R.K.-K. Far, H. Notbohm, N. Hunzelmann, and J. Brinckmann. 2006. Functional diversity of lysyl hydroxylase 2 in collagen synthesis of human dermal fibroblasts. Experimental Cell Research. 312:3485-3494.
Hyry et al. 2009. Missense Mutations that cause bruck syndrome affect enzymatic activity,folding and oligomerization of lysyl hydrozylase 2. Journal of Biological Chemistry, 284:30917-30924.
Koss et al. 1965. Wound healing an collagen formation. The Journal of Cell Biology. 27:83-106.
Olsen et al. 1974. Ferritin-conjugated antibodies used for labeling of organelles involved in the cellular synthesis and transport of procollagen. Proc Natl Acad Sci USA. 71:2033-2037.
Harwood et al. 1975. Studies on the glycosylation of hydroxylysine residues during collagen biosynthesis and the subcellular localization of collagen galactosyltransferase and collagen glucosyltransferase in tendon and cartilage cells. Biochem J. 152:291-302.
Ruotsalainen et al. 2001. Complete genomic structure of mouse lysyl hydroxylase 2 and lysyl hydroxylase 3/collagen glucosyltransferase. Matrix Biology. 20:137-146.
Ditto et al. 1974. Hydroxylation of peptide-bound proline and lysine before and after chain completion of the polypeptide chains of procollagen. Arch Biochem Biophys. 164:210-217.
PUBCHEM CID-42684328 Create Date: Jul. 20, 2009, pg. 1.
Krauth et al. "Synthesis and characterization of novel 1,2,4-triazine derivatives with antiproliferative activity", Bioorganic & Medicinal Chemistry, 2010, vol. 18, pp. 1816-1821.

*Primary Examiner* — Paul Zarek
(74) *Attorney, Agent, or Firm* — David M. Joyal; Juan M. McGillycuddy

(57) ABSTRACT

Methods for preventing, ameliorating, or reducing dermatological signs of aging are provided which employ cosmetic composition comprising novel active agents that enhance collagen production in the skin.

19 Claims, No Drawings

COLLAGEN STIMULATORS AND THEIR USE IN THE TREATMENT OF SKIN

FIELD OF INVENTION

The present invention relates generally to compounds, cosmetic formulations, and methods of improving the aesthetic appearance and health of human skin. In particular, the invention relates to compounds that promote the production of pro-collagen, collagen, and/or elastin in human skin.

BACKGROUND

Collagen is the body's major structural protein. It is composed of three protein chains wound together in a tight triple helix to form fibrils. The fibrils are cross-linked in the extracellular matrix to provide the structural scaffolding surrounding cells that helps to support cell shape and differentiation. The mesh-like collagen network binds cells together and provides the supportive framework or environment in which cells develop and function. The stimulation of collagen gives the skin its strength, durability, and smooth, plump appearance.

Collagen is created by fibroblasts, which are specialized skin cells located in the dermis, through a complex multistep process involving the hydroxylation of lysine residues in the nascent procollagen protein strands. The resultant hydroxylysyl groups aid in the formation of the triple helix and serve as attachment sites for cross linking in the extracellular matrix. See, Van der Slot et al., 2003, *J. Biol. Chem.*, 278: 40967-40972; Walker et al., 2005, *Matrix Biology*, 23:515-523; Wu et al., 2006, *Exp. Cell Res.*, 312:3485-3494. Thus, this modification is critical for the stability of procollagen, the intermolecular cross linking of collagen fibrils and ultimately the maintenance of the dermal matrix.

There is a continuing need for agents that stimulate pro-collagen and/or collagen production in human skin. It is therefore an object of the invention to provide new compounds, cosmetic formulations thereof, and methods for stimulating procollagen and/or collagen production in human skin. It is a further object of the invention to provide methods for improving the overall appearance of skin, including treating, reversing, reducing, forestalling and/or preventing signs of aging, such as skin wrinkles and fine lines, sagging skin, and/or thinning skin by stimulating procollagen and/or collagen production.

The foregoing discussion is presented solely to provide a better understanding of the nature of the problems confronting the art and should not be construed in any way as an admission as to prior art.

SUMMARY OF THE INVENTION

In accordance with the foregoing objectives and others, the present invention provides compounds and cosmetic formulations thereof that improve one or more signs of dermatological aging when topically applied to human integuments (skin, lips, nails, hair, etc.), particularly skin. The compounds of the invention lead to increased pro-collagen and/or collagen production within dermal fibroblasts and therefore will have a beneficial effect on reducing the appearance of aging on skin.

In one aspect of the invention, cosmetic compositions are provided for improving the aesthetic appearance of human skin comprising a cosmetically acceptable vehicle, and an effective amount of an active agent that stimulates pro-collagen and/or collagen production in the skin. The compounds of the invention will have a structure according to Formula I(a):

$$I(a)$$

Q represents a 3-6 membered heterocyclic ring, wherein $L_1$ and $L_2$ are independently selected from a bond or a group $\epsilon_1$-$(L_3)_l$-$\epsilon_2$, where "l" is an integer from 0 to 4; where $L_3$ is selected from —$CH_2$—, —CHR*—, —C(R*)$_2$—, —CH—, —CR*—, or a bond; and $\epsilon_1$ and $\epsilon_2$ are independently selected from —N—, —NH—, —NR$^N$—, —O—, —S—, —(C=O)—, or a bond; Y is selected from —CH—, —CR*—, —CHR*—, —C(R*)$_2$—, —N—, —O—, —S—, —NR$^N$—, or a bond (i.e. absent);

$Z_1$ represents a bond, —$CH_2$—, or —(C=O)—;

$Z_2$ represents a bond, —O—, NH—, —NR$^N$—, —$CH_2$—, —CHR*—, —C(R*)$_2$—, —(CH$_2$)$_p$—, —(CH$_2$)$_p$—NH, or —(CH$_2$)$_p$—NR$^N$—, where p is an integer from 1-6;

$X_1$ represents —$CH_2$—, —CHR*—, —C(R*)$_2$—, —NH—, —NR$^N$—, —O—, or —S—;

$X_2$ and $X_3$ represents nitrogen, —CH—, or —CR*—;

$R_1$-$R_5$ are independently selected, at each occurrence, from a group R; wherein R is selected from hydrogen, —F; —Cl; —Br, —I; —OH, —OR*; —NH$_2$; —NHR*; —N(R*)$_2$; —N(R*)$_3$$^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2$$^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3$$^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic C$_1$-C$_{12}$ hydrocarbon radical; a C$_1$-C$_{12}$ aromatic hydrocarbon radical; or a C$_1$-C$_{12}$ heteroaryl radical; where R* is independently at each occurrence hydrogen or a straight chained, branched, or cyclic C$_1$-C$_{20}$ hydrocarbon radical, which may be saturated, partially saturated, or aromatic, each of which may be optionally substituted with 1-6 heteroatoms selected from nitrogen, oxygen, sulfur, or halogen;

R$^N$ is hydrogen or a straight chained, branched, or cyclic saturated, partially saturated, or aromatic C$_1$-C$_{20}$ hydrocarbon radical, optionally substituted with 1-6 heteroatoms selected from nitrogen, oxygen, sulfur, or halogen; and cosmetically acceptable salts of the compounds of Formula I(a).

In some embodiments of the compounds of Formula I(a), $L_1$ is —(CH$_2$)$_m$—, and/or $L_2$ is —(CH$_2$)$_n$—, wherein "m" and "n" are independently selected from integers from 1-3; and Y is selected from —N—, —NR$^N$—, —S—, —O—, or a bond. In other embodiments, Q defines a heterocycle selected from the group consisting of aziridine, diaziridine, oxaziridine, azetidine, diazetidine, oxazetidine, pyrrolidine, oxazolidine, thiazolidine, imidazolidine, pyrazolidine, pyrrole, imidazole, pyrazole, 1,3,4-triazole, 1,2,3-triazole, piperidine, 4-alkyl-piperidine, morpholino, piperazine, and thiomorpholine, each being optionally substituted with one or more groups R. For example, Q may be a heterocycle selected from the group consisting of pyrrolidine, piperidine, morpholino, and piperazine, each being optionally substituted with one or more groups R (e.g., methyl). In one illustrative embodiment, ring Q is 4-methyl-piperidine.

In some embodiments of the compounds of Formula I(a), $Z_1$ is a bond (i.e., it is altogether absent) or —CH$_2$—; and $Z_2$ is a bond, —NH— or —CH$_2$—. In other embodiments of the compounds of Formula I(a), $Z_1$ is —CH$_2$—; and $Z_2$ is —CH$_2$—. In other embodiments of the compounds of Formula I(a), $X_1$ may be —NH— or —NR$^N$—; and/or $X_2$ and $X_3$ may be nitrogen. Typically (but not necessarily) $R_1$, $R_4$, and/or $R_5$ are hydrogen; and $R_2$ and/or $R_3$ may be a group —OR*, where R* is $C_{1-6}$alkyl. In one implementation, $R_2$ and/or $R_3$ are a group —OCH$_3$. In one illustrative embodiment, $Z_1$ is —CH$_2$—; $Z_2$ is —CH$_2$—; $X_1$ is —NH—; and $X_2$ and $X_3$ are each nitrogen.

In another aspect of the invention, cosmetic compositions are provided comprising a compound having the structure of Formula I(b):

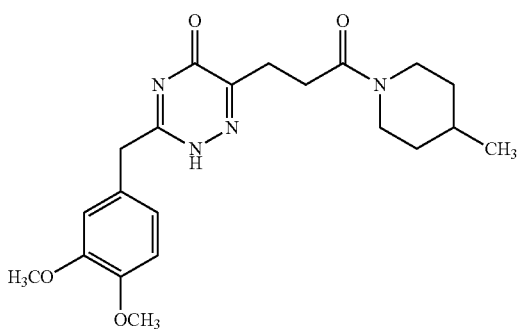

I(b)

and salts (e.g., acid addition salts) thereof.

The compounds of Formulas I(a) and I(B) may be formulated in cosmetically acceptable vehicles, which may comprises one or more of a film forming polymer, a thickener, a pH adjuster, a preservative, an emulsifier, a gelling agent, an antioxidant, a fragrance, a colorant, and the like. The vehicle may comprise a water-in-oil, oil-in-water, silicone-in-water, or water-in-silicone emulsion and will typically further comprise an emulsifier. The effective amount of the compound will typically be from about 0.00001% to about 1% (more typically, from 0.001% to about 0.5%) by weight of the composition. The formulations may optionally include a retinoid, for example retinoic acid, retinol, retinal, retinyl acetate, fatty acid esters of retinol, such as retinyl palmitate, to name a few.

In another aspect of the invention, a method is provided for improving the aesthetic appearance of human skin comprising topically applying to an area of the skin in need thereof a composition comprising an effective amount of a compound of Formula I(a) or I(b), for a time sufficient to improve the aesthetic appearance of said human skin. The aesthetic improvement of human skin may be an improvement of any attribute or characteristic of skin, including without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

In one embodiment of the invention, an inventive compound may be identified as CAS #1107720-70-6.

In a related implementation, a method is provided for the treatment of wrinkles and/or fine lines on the skin human skin (typically, skin of the face) comprising topically applying to an area of the skin in need thereof (e.g., applying to a wrinkle or fine line) a composition of Formulas I(a) or I(b), for a time sufficient to improve the aesthetic appearance of said human skin. The treatment may be a least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid) in amounts effective to improve the appearance of skin.

In a related aspect, methods are provided for enhancing the production of collagen or pro-collagen in human skin comprising topically applying to an area of the skin in need thereof (e.g., sagging skin, thinning skin, skin suffering from wrinkles and fine lines, etc.) a topical composition comprising a cosmetically acceptable vehicle, and an effective amount of a compound of Formulas I(a) or I(b), for a time sufficient to improve the appearance thereof. The treatment may be a least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid) in amounts effective to improve the appearance of skin.

In yet another aspect of the invention, methods are provided for reducing the severity of, reducing the number of, or preventing or forestalling the onset of, wrinkles or fine lines on human skin comprising topically applying to an area of the skin in need thereof (e.g., wrinkled skin), an effective amount (e.g., 0.0001%-1% by weight, w/w) of a compound of Formulas I(a) or I(b) in combination with an effective amount (e.g., 0.01%-5% by weight, w/w) of retinol and/or an effective amount (e.g., 0.001%-5% by weight, w/w) of an alpha-hydroxy acid (e.g., glycolic acid) and/or a beta-hydroxy acid (e.g., salicylic acid). The treatment may be a least once or twice daily and may last for a period of at least four weeks, typically at least eight weeks or longer.

Further aspects, features and advantages of the present invention will be better appreciated upon a reading of the following detailed description of the invention and claims.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Therefore, specific structural and functional details disclosed herein are not to be interpreted as limiting, but merely as a representative basis for teaching one skilled in the art to variously employ the present invention.

All terms used herein are intended to have their ordinary meaning unless otherwise provided. By "cosmetically acceptable," it is meant that a particular component is generally regarding as safe and non-toxic at the levels employed. The term "prevent," as used herein, includes delaying the onset of or progression of a particular sign of skin aging. The term "thin skin" includes skin that becomes thinner with chronological aging as well as prematurely thinned skin, which may be caused, for example, by photo-aging. In one embodiment, the prematurely thinned skin has been diagnosed as such by a clinician. The phrase "individual in need thereof" refers to a human that could benefit from improved dermal appearance or health, including males or females. In some embodiments, the individual in need thereof is a female. The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification.

The compounds of the invention improve the appearance of human skin. Without wishing to be bound by any particular theory, it is believed that they do so by stimulating the production of pro-collagen and/or collagen in the skin. The compounds of the invention generally have a structure according to Formula I(a):

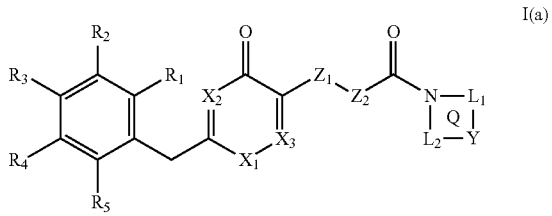

I(a)

Q represents a 3-6 membered heterocyclic ring, wherein $L_1$ and $L_2$ are independently selected from a bond or a group $\epsilon_1$-$(L_3)_l$-$\epsilon_2$, where "l" is an integer from 0 to 4 (including 0, 1, 2, 3, and 4); where $L_3$ is selected from —$CH_2$—, —$CHR^*$—, —$C(R^*)_2$—, —CH—, —$CR^*$—, or a bond; and $\epsilon_1$ and $\epsilon_2$ are independently selected from —N—, —NH—, —$NR^N$—, —O—, —S—, —(C=O)—, or a bond; and in one embodiment, $L_3$ is —$CH_2$— and l is an integer 1, 2, or 3, including an embodiment where $L_3$ is —$CH_2$— where l is 2 and $\epsilon_1$ and $\epsilon_2$ are both a bond (i.e., absent) such that the groups $L_1$ and/or $L_2$ have the form —$CH_2$—$CH_2$—; and in a particular embodiment, $L_1$ and $L_2$ both have the form —$CH_2$—$CH_2$—, although any of the hydrogens in the etheylene radical may be optionally substituted with groups R (e.g., with methyl, etc.);

Y is selected from —CH—, —$CR^*$—, —$CHR^*$—, —$C(R^*)_2$—, —N—, —O—, —S—, —$NR^N$—, or a bond (i.e., absent); but is typically —CH— or —$CR^*$—, where $R^*$ is as defined above, with special mention being made of lower alkyl (i.e., methyl, ethyl, propyl, isopropyl, butyl, etc.).

$Z_1$ represents a bond, —$CH_2$—, or —(C=O)—; and is typically (but not necessarily) —$CH_2$—; $Z_2$ represents a bond, —O—, NH—, —$NR^N$—, —$CH_2$—, —$CHR^*$—, —$C(R^*)_2$—, —$(CH_2)_p$—, —$(CH_2)_p$—NH, or —$(CH_2)_p$—$NR^N$—, where p is an integer from 1-6; and is typically (but not necessarily) —$CH_2$—. In one embodiment, $Z_1$ and $Z_2$ together form —$CH_2$—$CH_2$—, although any of the hydrogens in the etheylene radical may be optionally substituted with groups R (e.g., with methyl, etc.);

$X_1$ represents —$CH_2$—, —$CHR^*$—, —$C(R^*)_2$—, —NH—, —$NR^N$—, —O—, or —S—; and in some embodiments, $X_1$ represents —NH— or —$NR^N$—, where $R^N$ is as defined above, with special mention being made of lower alkyl (i.e., methyl, ethyl, propyl, isopropyl, butyl, etc.). $X_2$ and $X_3$ may be independently selected from nitrogen atoms, —CH—, and —$CR^*$—. In one embodiment, $X_2$ and/or $X_3$ are nitrogen atoms.

$R_1$-$R_5$ are independently selected, at each occurrence, from a group R; wherein R is selected from hydrogen, —F; —Cl; —Br, —I; —OH, —$OR^*$; —$NH_2$; —$NHR^*$; —$N(R^*)_2$; —$N(R^*)_3^+$; —$N(R^*)$—OH; —N(→O)$(R^*)_2$; —O—$N(R^*)_2$; —$N(R^*)$—O—$R^*$; —$N(R^*)$—$N(R^*)_2$; —C=N—$R^*$; —N=$C(R^*)_2$; —C=N—$N(R^*)_2$; —C(=$NR^*$)—$N(R^*)_2$; —SH; —$SR^*$; —CN; —NC; —(C=O)—$R^*$; —CHO; —$CO_2H$; —$CO_2^-$; —$CO_2R^*$; —(C=O)—S—$R^*$; —O—(C=O)—H; —O—(C=O)—$R^*$; —S—(C=O)—$R^*$; —(C=O)—$NH_2$; —(C=O)—$N(R^*)_2$; —(C=O)—$NHNH_2$; —O—(C=O)—$NHNH_2$; —(C=S)—$NH_2$; —(C=S)—$N(R^*)_2$; —$N(R^*)$—CHO; —$N(R^*)$—(C=O)—$R^*$; —(C=NR)—O—$R^*$; —O—(C=$NR^*$)—$R^*$, —SCN; —NCS; —NSO; —$SSR^*$; —$N(R^*)$—C(=O)—$N(R^*)_2$; —$N(R^*)$—C(=S)—$N(R^*)_2$; —$SO_2$—$R^*$; —O—S(=O)$_2$—$R^*$; —$S(=O)_2$—$OR^*$; —$N(R^*)$—$SO_2$—$R^*$; —$SO_2$—$N(R^*)_2$; —O—$SO_3^-$; —O—S(=O)$_2$—$OR^*$; —O—S(=O)—$OR^*$; —O—S(=O)—$R^*$; —S(=O)—$OR^*$; —S(=O)—$R^*$; —NO; —$NO_2$; —$NO_3$; —O—NO; —O—$NO_2$; —$N_3$; —$N_2$—$R^*$; —$N(C_2H_4)$; —$Si(R^*)_3$; —$CF_3$; —O—$CF_3$; —$PR^*_2$; —O—P(=O)$(OR^*)_2$; —P(=O)$(OR^*)_2$; perfluoroalkyl; an aliphatic $C_1$-$C_{12}$ hydrocarbon radical; a $C_1$-$C_{12}$ aromatic hydrocarbon radical; or a $C_1$-$C_{12}$ heteroaryl radical; where $R^*$ is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, or halogen;

$R^N$ is hydrogen or a straight chained, branched, or cyclic saturated, partially saturated, or aromatic $C_1$-$C_{20}$ hydrocarbon radical, optionally substituted with 1-6 heteroatoms selected from nitrogen, oxygen, sulfur, or halogen; and cosmetically acceptable salts of the compounds of Formula I(a).

In some embodiments of the compounds of Formula I(a), $L_1$ is —$(CH_2)_m$—, and/or $L_2$ is —$(CH_2)_n$—, wherein "m" and "n" are independently selected from integers from 1-3; and Y is selected from —N—, —$NR^N$—, —S—, —O—, or a bond.

In other embodiments, Q defines a heterocycle selected from the group consisting of aziridine, diaziridine, oxaziridine, azetidine, diazetidine, oxazetidine, pyrrolidine, oxazolidine, thiazolidine, imidazolidine, pyrazolidine, pyrrole, imidazole, pyrazole, 1,3,4-triazole, 1,2,3-triazole, piperidine, 4-alkyl-piperidine, morpholino, piperazine, and thiomorpholine, each being optionally substituted with one or more groups R. For example, Q may be a heterocycle selected from the group consisting of pyrrolidine, piperidine, morpholino, and piperazine, each being optionally substituted with one or more groups R (e.g., methyl). In one illustrative embodiment, ring Q is 4-methyl-piperidine.

In some embodiments of the compounds of Formula I(a), $Z_1$ is a bond (i.e., it is altogether absent) or —$CH_2$—; and $Z_2$ is a bond, —NH— or —$CH_2$—. In other embodiments of the compounds of Formula I(a), $Z_1$ is —$CH_2$—; and $Z_2$ is —$CH_2$—. In other embodiments of the compounds of Formula I(a), $X_1$ may be —NH— or —$NR^N$—; and/or $X_2$ and/or $X_3$ may be nitrogen. Typically (but not necessarily) $R_1$, $R_4$, and/or $R_5$ are hydrogen; and $R_2$ and/or $R_3$ may be a group —OR*, where R* is $C_{1-6}$ alkyl. In one implementation, $R_2$ and/or $R_3$ are a group —$OCH_3$. In one illustrative embodiment, $Z_1$ is —$CH_2$—; $Z_2$ is —$CH_2$—; $X_1$ is —NH—; and $X_2$ and $X_3$ are each nitrogen.

The invention embraces the use of cosmetically or pharmaceutically acceptable (e.g., non-toxic and/or non-irritating) salts of the compounds of Formula I(a). Examples of the salts of the compounds in the present invention include salts with alkali metals such as sodium and potassium; salts with alkaline-earth metals such as calcium and magnesium; salts with amines such as monoethanolamine; salts with inorganic acids such as hydrochloric acid and sulfuric acid; and salts with organic acids such as citric acid and acetic acid. Special mention may be made of acid addition salts and in particular hydrochloride salts.

In another aspect of the invention, cosmetic compositions are provided comprising a compound (or salt thereof) having the structure I(b):

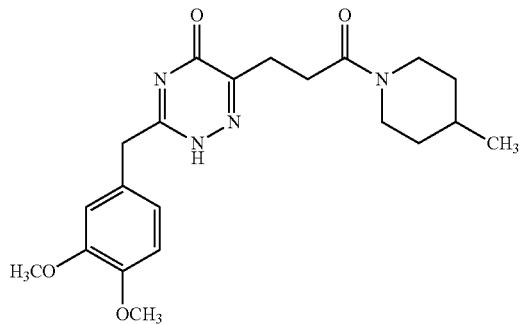

The compounds of Formula I(a) or I(b) may be racemic or may comprise and enantiomeric excess of either the R or S enantiomer at the stereocenter defined by the point of attachment of the methyl group to the piperidinyl ring. In some embodiments, the compound comprise and enantiomeric excess of at least about 90% of the R enantiomer; in other embodiments the compound comprises an enantiomeric excess of at least about 90% of the S enantiomer. In some embodiments, the methyl group on the piperidinyl ring may be replaced by hydrogen, trifluoromethyl, ethyl, methoxy, amino, trimethylamino, carboxy, or cyano groups.

The compounds of Formulas I(a) and I(b) may be formulated in cosmetically acceptable vehicles, which may comprises one or more of a film forming polymer, a thickener, a pH adjuster, a preservative, an emulsifier, a gelling agent, an antioxidant, a fragrance, a colorant, and the like. The vehicle may comprise a water-in-oil, oil-in-water, silicone-in-water, or water-in-silicone emulsion and will typically further comprise an emulsifier. The effective amount of the compound will typically be from about 0.00001% to about 1% (more typically, from 0.001% to about 0.5%) by weight of the composition. The formulations may optionally include a retinoid, for example retinoic acid, retinol, retinal, retinyl acetate, fatty acid ester of retinol, such as retinyl palmitate, to name a few.

In another aspect of the invention, a method is provided for improving the aesthetic appearance of human skin comprising topically applying to an area of the skin in need thereof a composition comprising an effective amount of a compound of Formula I(a) or I(b), for a time sufficient to improve the aesthetic appearance of said human skin.

In a related implementation, a method is provided for the treatment of wrinkles and/or fine lines on the skin human skin (typically, skin of the face) comprising topically applying to an area of the skin in need thereof (e.g., applying to a wrinkle or fine line) a composition of Formulas I(a) or I(b), for a time sufficient to improve the aesthetic appearance of said human skin. The treatment may be a least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid) in amounts effective to improve the appearance of skin.

In a related aspect, methods are provided for enhancing the production of collagen or pro-collagen in human skin comprising topically applying to an area of the skin in need thereof (e.g., sagging skin, thinning skin, skin suffering from wrinkles and fine lines, etc.) a topical composition comprising a cosmetically acceptable vehicle, and an effective amount of a compound of Formulas I(a) or I(b), for a time sufficient to improve the appearance thereof. The treatment may be a least once or twice daily and may last for a period of at least four weeks, typically at least eight weeks or longer. The composition may optionally further comprise a retinoid and/or an alpha-hydroxy acid (e.g., glycolic acid) and/or a beta-hydroxy acid (e.g., salicylic acid) in amounts effective to improve the appearance of skin.

In yet another aspect of the invention, methods are provided for reducing the severity of, reducing the number of, or preventing or forestalling the onset of, wrinkles or fine lines on human skin comprising topically applying to an area of the skin in need thereof (e.g., wrinkled skin), an effective amount (e.g., 0.0001%-1% by weight, w/w) of a compound of Formulas I(a) or I(b) in combination with an effective amount (e.g., 0.01%-5% by weight, w/w) of retinol and/or an effective amount (e.g., 0.001%-5% by weight, w/w) of an alpha-hydroxy acid (e.g., glycolic acid) and/or a beta-hydroxy acid (e.g., salicylic acid). The treatment may be a least once or twice daily and may last for a period of at least four weeks, typically at least eight weeks or longer.

The cosmetic compositions of this invention may further comprise a retinoid. Retinoids may be without limitation retinol (Vitamin A) and esters thereof, such as retinol palmitate, retinol acetate and retinol propionate, and salts thereof, retinaldehyde, or retinoic acid (e.g., all-trans or 13-cis) and derivatives thereof. The cosmetic compositions of this invention may further comprise alpha-hydroxy acids, such as glycolic acid, or beta hydroxyl acids, such as salicylic acid.

The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more.

The aesthetic improvement of human skin may be an improvement of any attribute or characteristic of skin (including reduction in one or more dermatological signs of aging), including without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

In practice, the compositions of the invention may be applied, alone or in cosmetically acceptable vehicles, to skin in need of treatment. That is, skin which suffers from a deficiency or loss in any of the foregoing attributes or which would otherwise benefit from improvement in any of the foregoing skin attributes. The skin is typically treated once or twice daily. The treatment may continue for a week, two weeks, four weeks, eight weeks, six months or longer.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, §201(i).

In one embodiment the active agents are topically applied, in a cosmetically acceptable vehicle, to skin suffering from fine lines and/or wrinkles to prevent, treat, and/or ameliorate the appearance of the fine lines and/or wrinkles in the skin. In this case, the compositions are applied to skin in need of treatment, by which is meant skin already having wrinkles and/or fine lines or skin that is at risk of developing fine lines and/or wrinkles. The compositions may be applied directly to the fine lines and/or wrinkles on the skin of the face, neck, lips, chest, and/or hands. The compositions or compounds can remediate signs of aging, including wrinkles and fine lines, by enhancing production of procollagen and/or collagen in skin.

In one embodiment, the invention is directed to a method of improving the aesthetic appearance of skin by increasing the production of collagen in the skin, the method comprising topically applying to an area of the skin in need thereof an effective amount of a compound according to Formula I(a), including the compound according to Formula I(b), and in each case, topically acceptable acid addition salts thereof.

The cosmetic compositions according to the invention can be formulated in a variety of forms for topical application and will comprise from about 0.00001% to about 90% by weight of a compound of Formula I(a) or I(b), and typically will comprise such actives in an amount from about 0.0001% to about 25% by weight, and more typically from about 0.001% to about 10% by weight. In some embodiments, the compounds of Formula I(a) or I(b) will individually or collectively comprise from 0.01% to about 5% by weight of the composition. When the cosmetic compositions according to the invention are formulated in a liquid form, they typically will be present at a concentration from about 0.001 $\mu$M to about 50 $\mu$M, or from about 0.5 $\mu$M to about 10 $\mu$M, or from about 2.25 $\mu$M to about 10 $\mu$M.

The compositions can include a cosmetically acceptable vehicle. Such vehicles may take the form of any known in the art suitable for application to skin and may include, but are not limited to, water, vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The vehicle may comprise an aqueous phase, an oil phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a nonionic, anionic or amphoteric surfactant, or a gelling agent.

In one embodiment, the topical composition will have a pH range from 1 to 8, with a pH in the range of from 2 to 7 being typical. In some embodiment, the composition will have a pH in the range of from 3.5 to 5.5. Suitable pH adjusters such as citric acid and triethanolamine may be added to bring the pH within the desired range. In one embodiment, the pH of the cosmetic formulation is maintained at or below about 4.0 so as to enhance retinoid stability.

In one embodiment of the invention, the compositions may include additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; thiodipropionic acid (TDPA) and esters thereof; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans or 13-cis), and derivatives thereof, retinaldehyde, retinol (Vitamin A) and esters thereof, such as retinol palmitate, retinol acetate and retinol propionate, and salts thereof. Particular mention may be made of retinol. It is contemplated that combinations of the compounds of Formula I(a) or I(b) with any of these retinoids will provide enhanced or synergistic improvements to skin. The retinoids will typically be included in amounts from about 0.0001% to about 5% by weight, more typically from about 0.01% to about 2.5% by weight, or from about 0.1% to about 1.0% by weight. Compositions according to this embodiment may typically include an antioxidant such as ascorbic acid and/or BHT and/or a chelating agent such as EDTA or a salt thereof.

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.01% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. In one particular embodiment, the inventive compositions will include a combination of retinol, TDPA or an ester thereof (notably, dilauryl thiodipropionic acid), and an alpha hydroxyl acid (glycolic acid) and/or beta hydroxyl acid (salicylic acid). Compositions of the present invention may comprise an antioxidant, which may comprise from about 0.001 wt % to about 10 wt %, or from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents; metal chelating agents such as EDTA or salts thereof; pigments; colorants; and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. The composition is typically formulated as an emulsion, lotion, cream, ointment, serum or gel.

The invention provides a method for treating aging skin by topically applying a composition comprising a collagen-stimulating compound of Formula I(a) or I(b), typically in a cosmetically acceptable vehicle, over the affected area for a period of time sufficient to remediate, reverse, reduce, ameliorate, or prevent dermatological signs of aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof. In some embodiments, each of the forgoing is associated with female skin.

In some embodiments, the compounds of Formulas I(a) or I(b) will be used to reduce the severity of fine lines or wrinkles, often in combination with retinol. The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the cosmetic compositions of the invention will be applied to the skin in an amount from about 0.001 to about 100 mg/cm$^2$, more typically from about 0.01 to about 20 mg/cm$^2$, or from about 0.1 to about 10 mg/cm$^2$.

It is also contemplated that the compositions of the invention will be useful for treating thin skin by topically applying the composition to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

In one embodiment, the compositions of the invention are applied to human skin to reduce sebum production or improve the appearance of skin affected by cellulite, and/or reduce unwanted lipogenesis or increase lipolysis. In this embodiment, the compounds of Formulas I(a) or I(b) can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, perilla oil and other unsaturated fatty oils and omega-3 fatty acids such as alpha-linolenic acid; caffeine; theophylline; xanthines; retinoids (e.g., retinol); and the like. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer.

In another embodiment, the compositions of the invention are applied to human skin for depigmentation, including to reduce areas of unwanted pigmentation, such as hyperpigmentation, including age spots and freckles. In this embodiment, the compounds of Formulas I(a) or I(b) can be formulated in cosmetically acceptable vehicles (as described herein) and may include one or more additional agents that combat pigmentation or hyperpigmentation, including tyrosinase inhibitors and/or melanosome transfer inhibitors. Special mention may be made of thiodipropionic acid and esters thereof (notably, di-lauryl esters); hydroquinone and the monobenzyl ether thereof; hydroquinone-beta-D-glucopyranoside; retinoids (e.g., retinoic acid); tretinoin; azelaic acid; Kojic acid (5-hydroxy-4-pyran-4-one-2-methyl); Mequinol (4-hydroxyanisole); Niacinamide; soy protein and other serine protease inhibitors; paper mulberry extract; Glabridin (licorice extract); *Arctostaphylos patula* and *Arctostaphylos viscida* extracts; Magnesium-L-ascorbyl-2-phosphate (MAP); 4-Isopropylcatechol; Aleosin; N-acetyl-4-S-cysteaminylphenol and N-propionyl-4-S-cysteaminylphenol; N-acetyl glucosamine; and Tranexamic acid (trans-4-aminomethylcyclohexanecarboxylic acid); to name a few.

In another embodiment, the compounds of Formulas I(a) and I(b) are intended for oral use, including for pharmaceutical use. Pharmaceutical formulations will include pharmaceutically acceptable carriers (i.e., diluents and excipients). The pharmaceutical compositions may be included in solid dosage forms, including compressed tablets and capsules, or in liquid or powder forms. Pharmaceutical dosage forms will typically include from about 0.5 mg to about 200 mg, or from about 1 mg to about 100 mg of the compound of Formulas I(a) and I(b). The dosage forms may be immediate release, in which case they will typically comprise a water-soluble or dispersible carrier such as microcrystalline cellulose, mannitol, hydroxypropyl methyl cellulose, PVP or the like, or may be delayed, sustained, or modified release, in which case they may comprise water-insoluble polymers such as cellulose ethers (e.g., ethylcellulose), alone or in combination with water soluble or dispersible polymers, to regulate the rate of dissolution of the dosage form in the stomach.

EXAMPLES

The following example describes specific aspects of the invention to illustrate the invention but should not be construed as limiting the invention, as the example merely provide specific methodology useful in the understanding and practice of the invention and its various aspects.

Example 1

Stimulation of Collagen Production

Cell Treatment: Normal Human dermal fibroblasts were grown in DMEM (Mediatech; cat. #: 15-013-CV) containing 10% Fetal Bovine Serum (Perbio; cat. #: SH30070.03), Penicillin/Streptomycin (Mediatech, Cat #30-001-C1), L-Glutamine (Mediatech; cat. #: 25-005-CI) at 37° C. and 10% $CO_2$. Cells were stripped of serum overnight, followed by treatment with the compound of Formula I(b) (0.0005%) or vehicle (DMSO), in the absence of serum for 48 hours.

Procollagen Assay: Procollagen levels in conditioned media were determined using Procollagen Type-I C-Peptide EIA Kit from Takara; cat. #MK101 as per manufacturer's suggestion. Reading was measured at 450 nm using a spectrophotometer.

Results:

Human dermal fibroblasts treated with 0.0005% the compound of Formula I(b) for 48 hours were analyzed by ELISA for expression levels of pro-collagen. Cells treated with the compound of Formula I(b) demonstrated a significant increase in pro-collagen, relative to control, vehicle treated cells. All values are statistically significant at $p<0.05$.

TABLE 1

| Test Compound | Procollagen |
| --- | --- |
| Control | 100% |
| Formula I(b) (0.0005%) | 146% |

Collagen is a key building block of the dermis, and production of collagen decline with ages, and thus contributes to wrinkle formation. The data in Table 1 shows that the compound of Formula I(b) stimulates procollagen production and therefore would be expected to help increase skin's key building block, Collagen, and generate new collagen to help fill wrinkles.

Additional Embodiments

1. A cosmetic composition for improving the aesthetic appearance of human skin comprising a cosmetically acceptable vehicle, and an effective amount of a compound according to Formula I(a):

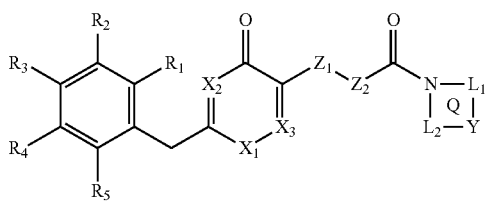

wherein,
Q represents a 3-6 membered heterocyclic ring, wherein $L_1$ and $L_2$ are independently selected from a bond or a group $\epsilon_1$-$(L_3)_l$-$\epsilon_2$, where "l" is an integer from 0 to 4; where $L_3$ is selected from —$CH_2$—, —CHR*—, —C(R*)$_2$—, —CH—, —CR*—, or a bond; and E and $\epsilon_2$ are independently selected from —N—, —NH—, —NR$^N$—, —O—, —S—, —(C=O)—, or a bond; Y is selected from —CH—, —CR*—, —CHR*—, —C(R*)$_2$—, —N—, —O—, —S—, —NR$^N$—, or a bond (i.e. absent);
$Z_1$ represents a bond, —$CH_2$—, or —(C=O)—;
$Z_2$ represents a bond, —O—, NH—, —NR$^N$—, —$CH_2$—, —CHR*—, —C(R*)$_2$—, —($CH_2$)$_p$—, —($CH_2$)$_p$—NH, or —($CH_2$)$_p$—NR$^N$—, where p is an integer from 1-6;
$X_1$ represents —$CH_2$—, —CHR*—, —C(R*)$_2$—, —NH—, —NR$^N$—, —O—, or —S—;
$X_2$ and $X_3$ represents nitrogen, —CH—, or —CR*—;
$R_1$-$R_5$ are independently selected, at each occurrence, from a group R; wherein R is selected from hydrogen, —F; —Cl; —Br; —I; —OH, —OR*; —$NH_2$; —NHR*; —N(R*)$_2$; —N(R*)$_3^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —$CO_2$H; —$CO_2^-$; —$CO_2$R*; —(C=O)—S—R*; —O—(C=O)—H; —O—(C=O)—R*; —S—(C=O)—R*; —(C=O)—$NH_2$; —(C=O)—N(R*)$_2$; —(C=O)—$NHNH_2$; —O—(C=O)—$NHNH_2$; —(C=S)—$NH_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S) —N(R*)$_2$; —$SO_2$—R*; —O—S(=O)$_2$—R*; —S(=O)$_2$—OR*; —N(R*)—$SO_2$—R*; —$SO_2$—N(R*)$_2$; —O—$SO_3^-$; —O—S(=O)$_2$—OR*; —O—S(=O)—OR*; —O—S(=O)—R*; —S(=O)—OR*; —S(=O)—R*; —NO; —$NO_2$; —$NO_3$; —O—NO; —O—$NO_2$; —$N_3$; —$N_2$—R*; —N($C_2H_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{12}$ hydrocarbon radical; a $C_1$-$C_{12}$ aromatic hydrocarbon radical; or a $C_1$-$C_{12}$ heteroaryl radical; where R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, or halogen;
$R^N$ is hydrogen or a saturated, partially saturated, or aromatic $C_1$-$C_{20}$ hydrocarbon radical, optionally substituted with 1-6 heteroatoms selected from nitrogen, oxygen, sulfur, or halogen;
and cosmetically acceptable salts thereof.

2. The cosmetic composition according to claim 1, wherein $L_1$ is —($CH_2$)$_m$—, and $L_2$ is —($CH_2$)$_n$—, wherein "m" and "n" are independently selected from integers from 1-3; and Y is selected from —N—, —NR$^N$—, —S—, —O—, or a bond.

3. The cosmetic composition according to claim 2, wherein ring Q is a heterocycle selected from the group consisting of aziridine, diaziridine, oxaziridine, azetidine, diazetidine, oxazetidine, pyrrolidine, oxazolidine, thiazolidine, imidazolidine, pyrazolidine, pyrrole, imidazole, pyrazole, 1,3,4-triazole, 1,2,3-triazole, piperidine, 4-alkyl-piperidine, morpholino, piperazine, and thiomorpholine, each being optionally substituted with one or more groups R.

4. The cosmetic composition according to claim 3, wherein ring Q is a heterocycle selected from the group consisting of pyrrolidine, piperidine, morpholino, and piperazine, each being optionally substituted with one or more groups R.

5. The cosmetic composition according to claim 4, wherein ring Q is 4-methyl-piperidine.

6. The cosmetic composition according to claim 1, wherein $Z_1$ is —$CH_2$— and $Z_2$ is —NH— or —$CH_2$—.

7. The cosmetic composition according to claim 1, wherein $X_1$ is —NH— or —NR$^N$—.

8. The cosmetic composition according to claim 1, wherein $X_2$ and $X_3$ are nitrogen.

9. The cosmetic composition according to claim 1, wherein $R_1$, $R_4$, and $R_5$ are hydrogen.

10. The composition according to claim 1, wherein $R_2$ and/or $R_3$ are a group —OR*, where R* is $C_{1-6}$alkyl.

11. The composition according to claim 9, wherein $R_2$ and $R_3$ are a group —$OCH_3$.

12. The composition according to claim 4, wherein $Z_1$ is —$CH_2$—; $Z_2$ is —$CH_2$—; $X_1$ is —NH—; and $X_2$ and $X_3$ are each nitrogen.

13. The composition according to claim 1, wherein the compound according to Formula I(a) has the structure of Formula I(b):

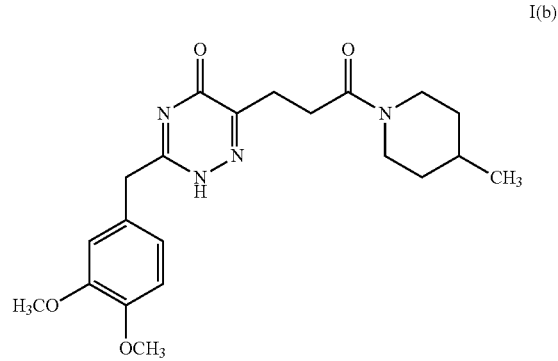 [SMILES: COc1ccc(Cc2nc(=O)c(CCC(=O)N3CCC(C)CC3)n[nH]2)cc1OC]

and cosmetically acceptable salts thereof.

14. The composition according to claim 1, wherein said cosmetically acceptable vehicle comprises one or more of a film forming polymer, a thickener, a pH adjuster, a preservative, an emulsifier, a gelling agent, an antioxidant, a fragrance, and a colorant.

15. The composition according to claim 1, wherein said cosmetically acceptable vehicle comprises a water-in-oil or oil-in-water emulsion and further comprises an emulsifier.

16. The composition according to claim 1, wherein said effective amount comprises from about 0.00001% to about 1% by weight of said composition.

17. The composition according to claim 1, further comprising a retinoid selected from the group consisting of retinoic acid, retinol, retinal, retinyl acetate, and retinyl palmitate.

18. A method for improving the aesthetic appearance of human skin comprising topically applying to an area of the skin in need thereof a composition according to claim 1, for a time sufficient to improve the aesthetic appearance of said human skin.

19. The method according to claim 18, wherein said aesthetic improvement of said human skin is selected from the group consisting of:
(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

20. A method for improving the aesthetic appearance of human skin comprising topically applying to an area of the skin in need thereof a composition according to claim 1, for a time sufficient to improve the aesthetic appearance of said human skin.

21. The method according to claim 20, wherein said aesthetic improvement of said skin is the treatment of wrinkles and/or fine lines on the skin, and wherein said method comprises topically applying the composition to affected skin of an individual in need thereof, at least once daily for a period of at least four weeks.

22. The method according to claim 20, wherein said aesthetic improvement of said skin is the treatment of wrinkles and/or fine lines on the skin, and wherein said method comprises topically applying the composition to affected skin of an individual in need thereof, at least once daily for a period of at least eight weeks.

23. A method for improving the aesthetic appearance of human skin comprising topically applying to an area of the skin in need thereof a topical composition comprising a cosmetically acceptable vehicle and an effective amount of a compound having the structure of Formula I(b):

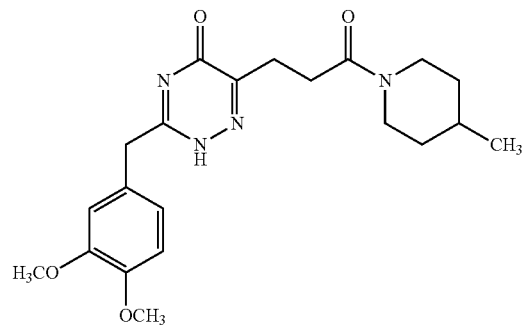

and cosmetically acceptable salts thereof, for a time sufficient to improve the aesthetic appearance of said human skin.

24. The method according to claim 23, wherein said aesthetic improvement of said human skin is selected from the group consisting of:
(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

25. The method according to claim 24, wherein said aesthetic improvement of said skin is the treatment of wrinkles and/or fine lines on the skin, and wherein said method comprises topically applying the composition to affected skin of an individual in need thereof, at least once daily for a period of at least four weeks.

26. The method according to claim 25, wherein said composition is topically applied to affected skin of an individual in need thereof at least once daily for a period of at least eight weeks.

27. The method according to claim 23, wherein said composition further comprises a retinoid.

28. The method according to claim 23, wherein said composition further comprises an alpha-hydroxy or beta-hydroxy acid.

29. The method according to claim 28, wherein said alpha-hydroxy acid is glycolic acid.

30. The method according to claim 28, wherein said beta-hydroxy acid is salicylic acid.

31. A method for enhancing the production of collagen in human skin comprising topically applying to an area of the skin in need thereof a topical composition comprising a cosmetically acceptable vehicle, and an effective amount of a compound having the structure of Formula I(b):

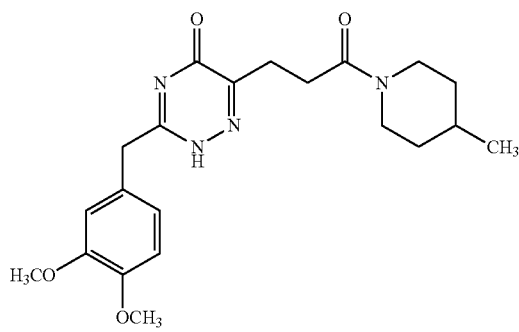

and cosmetically acceptable salts thereof.

32. The method according to claim 29, wherein said composition further comprises a retinoid.

33. The method according to claim 31, wherein said composition further comprises an alpha-hydroxy or beta-hydroxy acid.

34. The method according to claim 33, wherein said alpha-hydroxy acid is glycolic acid.

35. The method according to claim 33, wherein said beta-hydroxy acid is salicylic acid.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for reducing one or more dermatological signs of aging comprising topically applying to an area of the skin in need thereof a composition according to Formula I(a):

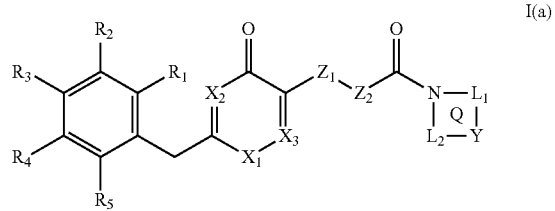

wherein,

Q represents a 3-6 membered heterocyclic ring, wherein $L_1$ and $L_2$ are independently selected from a bond or a group $\epsilon_1$-$(L_3)_l$-$\epsilon_2$, where "l" is an integer from 0 to 4; where $L_3$ is selected from —$CH_2$—, —$CHR^*$—, —$C(R^*)_2$—, —CH—, —$CR^*$—, or a bond; and $\epsilon_1$ and $\epsilon_2$ are independently selected from —N—, —NH—, —$NR^N$—, —O—, —S—, —(C=O)—, or a bond; Y is selected from —CH—, —$CR^*$—, —$CHR^*$—, —$C(R^*)_2$—, —N—, —O—, —S—, —$NR^N$—, or a bond (i.e. absent);

$Z_1$ represents a bond, —$CH_2$—, or —(C=O)—;

$Z_2$ represents a bond, —O—, NH—, —$NR^N$—, —$CH_2$—, —$CHR^*$—, —$C(R^*)_2$—, —$(CH_2)_p$—, —$(CH_2)_p$—NH, or —$(CH_2)_p$—$NR^N$—, where p is an integer from 1-6;

$X_1$ represents —$CH_2$—, —$CHR^*$—, —$C(R^*)_2$—, —NH—, —$NR^N$—, —O—, or —S—;

$X_2$ and $X_3$ represents nitrogen, —CH—, or —$CR^*$—;

$R_1$-$R_5$ are independently selected, at each occurrence, from a group R; wherein R is selected from hydrogen, —F; —Cl; —Br; —I; —OH, —$OR^*$; —$NH_2$; —$NHR^*$; —$N(R^*)_2$; —$N(R^*)_3^+$; —$N(R^*)$—OH; —N(→O)$(R^*)_2$; —O—$N(R^*)_2$; —$N(R^*)$—O—$R^*$; —$N(R^*)$—N$(R^*)_2$; —C=N—$R^*$; —N=C$(R^*)_2$; —C=N—$N(R^*)_2$; —C(=$NR^*$)—$N(R^*)_2$; —SH; —$SR^*$; —CN; —NC; —(C=O)—$R^*$; —CHO; —$CO_2H$; —$CO_2^-$; —$CO_2R^*$; —(C=O)—S—$R^*$; —O—(C=O)—H; —O—(C=O)—$R^*$; —S—(C=O)—$R^*$; —(C=O)—$NH_2$; —(C=O)—$N(R^*)_2$; —(C=O)—$NHNH_2$; —O—(C=O)—$NHNH_2$; —(C=S)—$NH_2$; —(C=S)—$N(R^*)_2$; —$N(R^*)$—CHO; —$N(R^*)$—(C=O)—$R^*$; —(C=NR)—O—$R^*$; —O—(C=$NR^*$)—$R^*$; —SCN; —NCS; —NSO; —$SSR^*$; —$N(R^*)$—C(=O)—$N(R^*)_2$; —$N(R^*)$—C(=S)—$N(R^*)_2$; —$SO_2$—$R^*$; —O—S(=O)$_2$—$R^*$; —S(=O)$_2$—$OR^*$; —$N(R^*)$—$SO_2$—$R^*$; —$SO_2$—N$(R^*)_2$; —O—$SO_3^-$; —O—S(=O)$_2$—$OR^*$; —O—S(=O)—$OR^*$; —O—S(=O)—$R^*$; —S(=O)—$OR^*$; —S(=O)—$R^*$; —NO; —$NO_2$; —$NO_3$; —O—NO; —O—$NO_2$; —$N_3$; —$N_2$—$R^*$; —$N(C_2H_4)$; —Si$(R^*)_3$; —$CF_3$; —O—$CF_3$; —$PR^*_2$; —O—P(=O)$(OR^*)_2$; —P(=O)$(OR^*)_2$; perfluoroalkyl; an aliphatic $C_1$-$C_{12}$ hydrocarbon radical; a $C_1$-$C_{12}$ aromatic hydrocarbon radical; or a $C_1$-$C_{12}$ heteroaryl radical; where $R^*$ is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, or halogen;

$R^N$ is hydrogen or a saturated, partially saturated, or aromatic $C_1$-$C_{20}$ hydrocarbon radical, optionally substituted with 1-6 heteroatoms selected from nitrogen, oxygen, sulfur, or halogen;

and cosmetically acceptable salts thereof;

for a time sufficient to improve the aesthetic appearance of said human skin.

2. The method according to claim 1, wherein said one or more dermatological signs of aging is selected from the group consisting of:
   (a) treatment, reduction, and/or prevention of fine lines or wrinkles;
   (b) reduction of skin pore size;
   (c) improvement in skin thickness, plumpness, and/or tautness;
   (d) improvement in skin smoothness, suppleness and/or softness;
   (e) improvement in skin tone, radiance, and/or clarity;
   (f) improvement in procollagen, and/or collagen production;
   (g) improvement in maintenance and remodeling of elastin;
   (h) improvement in skin texture and/or promotion of retexturization;
   (i) improvement in skin barrier repair and/or function;
   (j) improvement in appearance of skin contours;
   (k) restoration of skin luster and/or brightness;
   (l) replenishment of essential nutrients and/or constituents in the skin;
   (m) improvement of skin appearance decreased by aging and/or menopause;
   (n) improvement in skin moisturization;
   (o) increase in skin elasticity and/or resiliency;
   (p) treatment, reduction, and/or prevention of skin sagging;
   (q) improvement in skin firmness; and
   (r) reduction of pigment spots and/or mottled skin; and
   (s) improvement of optical properties of skin by light diffraction or reflection.

3. A method for improving one or more dermatological signs of aging comprising topically applying to an area of skin in need thereof a composition according to claim 1, for a time sufficient to improve said one or more dermatological signs of aging.

4. The method according to claim 3, wherein said one or more dermatological signs of aging comprises wrinkles and/or fine lines on the skin, and wherein said method comprises topically applying the composition to affected skin of an individual in need thereof, at least once daily for a period of at least four weeks.

5. The method according to claim 3, wherein said one or more dermatological signs of aging comprises wrinkles and/or fine lines on the skin, and wherein said method comprises topically applying the composition to affected skin of an individual in need thereof, at least once daily for a period of at least eight weeks.

6. A method for improving the one or more dermatological signs of aging comprising topically applying to an area of skin in need thereof a topical composition comprising a cosmetically acceptable vehicle and an effective amount of a compound having the structure of Formula I(b):

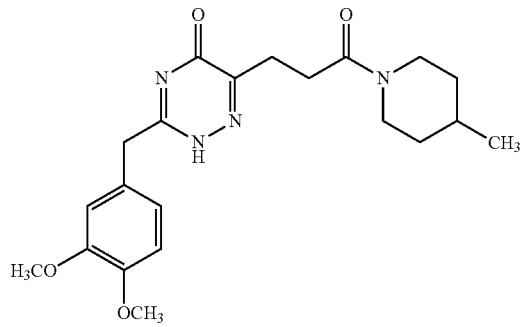

and cosmetically acceptable salts thereof, for a time sufficient to improve said one or more dermatological signs of aging.

7. The method according to claim 6, wherein said one or more dermatological signs of aging is selected from the group consisting of:
   (a) treatment, reduction, and/or prevention of fine lines or wrinkles;
   (b) reduction of skin pore size;
   (c) improvement in skin thickness, plumpness, and/or tautness;
   (d) improvement in skin smoothness, suppleness and/or softness;
   (e) improvement in skin tone, radiance, and/or clarity;
   (f) improvement in procollagen, and/or collagen production;
   (g) improvement in maintenance and remodeling of elastin;
   (h) improvement in skin texture and/or promotion of retexturization;
   (i) improvement in skin barrier repair and/or function;
   (j) improvement in appearance of skin contours;
   (k) restoration of skin luster and/or brightness;
   (l) replenishment of essential nutrients and/or constituents in the skin;
   (m) improvement of skin appearance decreased by aging and/or menopause;
   (n) improvement in skin moisturization;
   (o) increase in skin elasticity and/or resiliency;
   (p) treatment, reduction, and/or prevention of skin sagging;
   (q) improvement in skin firmness; and
   (r) reduction of pigment spots and/or mottled skin; and
   (s) improvement of optical properties of skin by light diffraction or reflection.

8. The method according to claim 7, wherein said one or more dermatological signs of aging comprises wrinkles and/or fine lines on the skin, and wherein said method comprises topically applying the composition to affected skin of an individual in need thereof, at least once daily for a period of at least four weeks.

9. The method according to claim 8, wherein said composition is topically applied to affected skin of an individual in need thereof at least once daily for a period of at least eight weeks.

10. The method according to claim 6, wherein said composition further comprises a retinoid.

11. The method according to claim 6, wherein said composition further comprises an alpha-hydroxy or beta-hydorxy acid.

12. The method according to claim 11, wherein said alpha-hydroxy acid is glycolic acid.

13. The method according to claim 11, wherein said beta-hydroxy acid is salicylic acid.

14. A method for enhancing the production of collagen in human skin comprising topically applying to an area of the skin in need thereof a topical composition comprising a cosmetically acceptable vehicle, and an effective amount of a compound having the structure of Formula I(b):

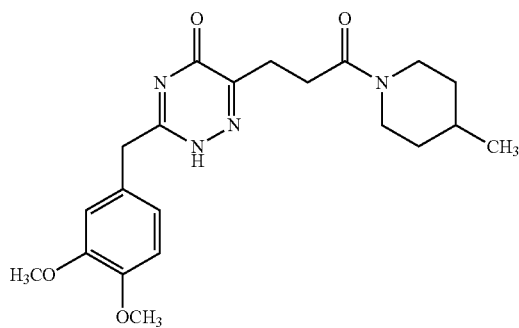

I(b)

and cosmetically acceptable salts thereof.

15. The method according to claim 12, wherein said composition further comprises a retinoid.

16. The method according to claim 14, wherein said composition further comprises an alpha-hydroxy or beta-hydorxy acid.

17. The method according to claim 16, wherein said alpha-hydroxy acid is glycolic acid.

18. The method according to claim 16, wherein said beta-hydroxy acid is salicylic acid.

19. A method for enhancing the production of collagen in human skin comprising topically applying to an area of the skin in need thereof a topical composition comprising a cosmetically acceptable vehicle, and an effective amount of a compound having the structure of Formula I(a):

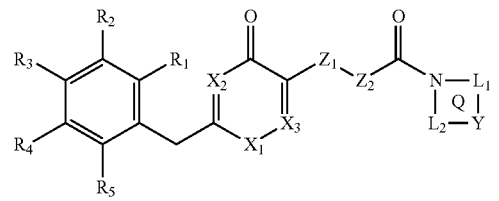

I(a)

wherein,

Q represents a 3-6 membered heterocyclic ring, wherein $L_1$ and $L_2$ are independently selected from a bond or a group $\epsilon_1$-$(L_3)_l$-$\epsilon_2$, where "l" is an integer from 0 to 4; where $L_3$ is selected from —$CH_2$—, —CHR*—, —C(R*)$_2$—, —CH—, —CR*—, or a bond; and $\epsilon_1$ and $\epsilon_2$ are independently selected from —N—, —NH—, —NR$^N$—, —O—, —S—, —(C=O)—, or a bond; Y is selected from —CH—, —CR*—, —CHR*—, —C(R*)$_2$—, —N—, —O—, —S—, —NR$^N$—, or a bond (i.e. absent);

$Z_1$ represents a bond, —$CH_2$—, or —(C=O)—;

$Z_2$ represents a bond, —O—, NH—, —NR$^N$—, —$CH_2$—, —CHR*—, —C(R*)$_2$—, —(CH$_2$)$_p$—, —(CH$_2$)$_p$—NH, or —(CH$_2$)$_p$—NR$^N$—, where p is an integer from 1-6;

$X_1$ represents —$CH_2$—, —CHR*—, —C(R*)$_2$—, —NH—, —NR$^N$—, —O—, or —S—;

$X_2$ and $X_3$ represents nitrogen, —CH—, or —CR*—;

$R_1$-$R_5$ are independently selected, at each occurrence, from a group R; wherein R is selected from hydrogen, —F; —Cl; —Br, —I; —OH, —OR*; —NH$_2$; —NHR*; —N(R*)$_2$; —N(R*)$_3$$^+$; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*)—N(R*)$_2$; —SH; —SR*; —CN; —NC; —(C=O)—R*; —CHO; —CO$_2$H; —CO$_2$$^-$; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —(C=NR)—O—R*; —O—(C=NR*)—R*, —SCN; —NCS; —NSO; —SSR*; —N(R*)—C(=O)—N(R*)$_2$; —N(R*)—C(=S)—N(R*)$_2$; —SO$_2$—R*; —O—S(=O)$_2$—R*; —S(=O)$_2$—OR*; —N(R*)—SO$_2$—R*; —SO$_2$—N(R*)$_2$; —O—SO$_3$$^-$; —O—S(=O)$_2$—OR*; —O—S(=O)—OR*; —O—S(=O)—R*; —S(=O)—OR*; —S(=O)—R*; —NO; —NO$_2$; —NO$_3$; —O—NO; —O—NO$_2$; —N$_3$; —N$_2$—R*; —N(C$_2$H$_4$); —Si(R*)$_3$; —CF$_3$; —O—CF$_3$; —PR*$_2$; —O—P(=O)(OR*)$_2$; —P(=O)(OR*)$_2$; perfluoroalkyl; an aliphatic $C_1$-$C_{12}$ hydrocarbon radical; a $C_1$-$C_{12}$ aromatic hydrocarbon radical; or a $C_1$-$C_{12}$ heteroaryl radical; where R* is independently at each occurrence hydrogen or a straight chained, branched, or cyclic $C_1$-$C_{20}$ hydrocarbon radical, which may be saturated, partially saturated, or aromatic, each of which may be optionally substituted with 1-6 heteroatoms selected from nitrogen, oxygen, sulfur, or halogen;

R$^N$ is hydrogen or a saturated, partially saturated, or aromatic $C_1$-$C_{20}$ hydrocarbon radical, optionally substituted with 1-6 heteroatoms selected from nitrogen, oxygen, sulfur, or halogen;

and cosmetically acceptable salts thereof.

* * * * *